United States Patent [19]
Choi

[11] Patent Number: 5,642,741
[45] Date of Patent: Jul. 1, 1997

[54] TOOTHPICK

[76] Inventor: Bongsik Choi, 120-214, Kwangan 1 Dong, Namgu, Pusan, Rep. of Korea

[21] Appl. No.: 548,372

[22] Filed: Nov. 1, 1995

[30] Foreign Application Priority Data

Nov. 1, 1994 [KR] Rep. of Korea ............... 94-28978

[51] Int. Cl.$^6$ .................................................. A61C 15/00
[52] U.S. Cl. ...................... 132/329; 132/321; 132/309; 132/328
[58] Field of Search .............................. 132/309, 321, 132/329, 323, 324, 325, 326, 327, 328; 15/167.1, 172, 184, 206, 111

[56] References Cited

U.S. PATENT DOCUMENTS

| | | | |
|---|---|---|---|
| 2,233,522 | 3/1941 | Fickle | 132/309 |
| 4,319,377 | 3/1982 | Tarrson et al. | 132/321 |
| 4,800,905 | 1/1989 | Stuart | 132/321 |
| 5,377,377 | 1/1995 | Bredall et al. | 132/321 |
| 5,488,751 | 2/1996 | Gekhter et al. | 132/321 |

FOREIGN PATENT DOCUMENTS 88-21409  12/1988  Rep. of Korea .

Primary Examiner—Gene Mancene
Assistant Examiner—Pedro Philogene
Attorney, Agent, or Firm—Lowe, Price, LeBlanc & Becker

[57] ABSTRACT

A toothpick is disclosed including an inter-teeth inserting portion in which a metal wire is formed to be spirally twisted and the overall circumferential surface is covered with synthetic resin; and a main body fixed to one end of said inter-teeth inserting portion for grasping.

12 Claims, 3 Drawing Sheets

TOOTHPICK

BACKGROUND OF THE INVENTION

The present invention is related to a toothpick. The toothpick prevents the gums from being damaged when food leftovers stuck between teeth are removed when using the toothpick. The toothpick is easy to carry and can be used repeatedly.

A conventional toothpick (not shown) consists of a cylindrical grasping portion and an interteeth inserting portion one or both ends of which are slant-angled and sharp-pointed. When removing food leftover between teeth using the conventional toothpick, the interteeth inserting portion is forcibly inserted between two teeth. Because of to the thickness of the toothpick the teeth's surrounding tissues are damaged and the spaces between teeth are widened. Repeated use of the conventional toothpick which causes the spaces between teeth to become larger will eventually increase the amount of food remaining between the teeth. Furthermore, due to the pointed end of the toothpick, the gums may be hurt if the pointed end is pushed into the gums causing their inflammation or odontological disease. An additional drawback of the conventional toothpick is that most of the toothpicks are mixed with food garbage after usage so that the food garbage is difficult to reuse as animal feed. For this reason, the food garbage is useless and will have a great influence on environmental pollution.

The amount of toothpicks used reaches thousands of ton for every year nationwide. Partly, toothpicks are imported from overseas. For the raw material of the toothpicks, tens of thousands of trees older than 10 years are required, thereby giving bad effect on earth warming prevention.

Accordingly, to solve the problems as above, Korean Laid-open Utility Model No. 88-21409 entitled "Interteeth Cleaner" discloses a device comprising a grip made of deformable elastic material and a central shaft with a tri-directional brush formed on one side of the grip. However, a process for making the brush onto the central shaft is difficult to perform, resulting in a higher production cost. Even in use, the space between teeth is not easily inserted by the brush formed on the central shaft, making it inconvenient. Further, the once-used interteeth cleaner does not easily remove the leftover stuck between teeth. Thus, this cannot be reused for sanitary reasons.

SUMMARY OF THE INVENTION

The object of the present invention, to solve the conventional problems above, is to provide a toothpick in which an interteeth inserting portion whose outer circumference is coated with synthetic resin is formed to prevent the gums from being hurted, a main body is formed for easy grasping to facilitate its usage, and a cap attached/separable from the main body is formed to facilitate carrying and keeping the toothpick sanitarily.

In order to accomplish the object of the present invention, there is provided a toothpick comprising: an inter-teeth inserting portion in which a metal wire is formed to be spirally twisted and the overall circumferential surface is covered with synthetic resin; and a main body fixed to one end of said inter-teeth inserting portion for grasping.

BRIEF DESCRIPTION OF THE ATTACHED DRAWINGS

DETAILED DESCRIPTION OF THE INVENTION

Figure 1:
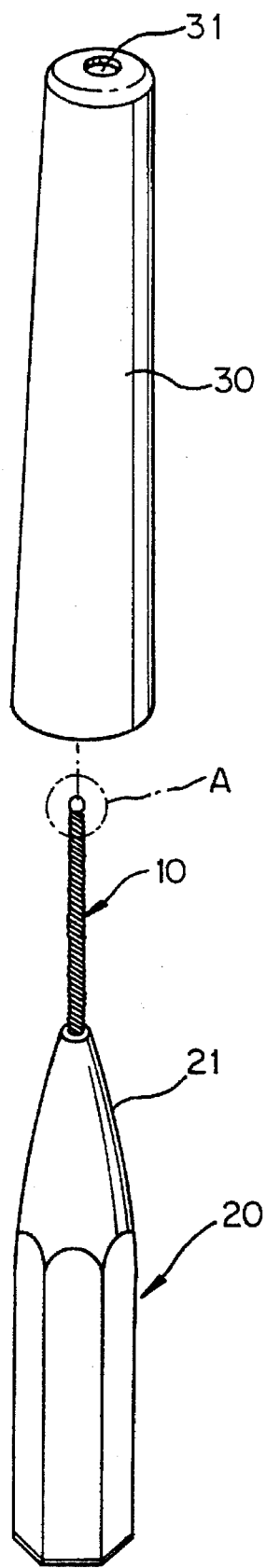
FIG. 1 is an exploded perspective view of the toothpick of the present invention.
Figure 2:
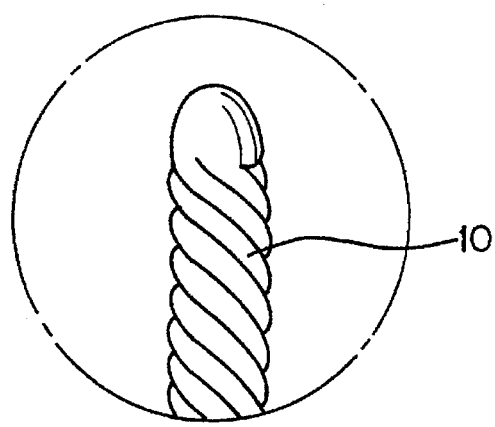
FIG. 2 is an enlarged view of portion A of FIG. 1.
Figure 3:
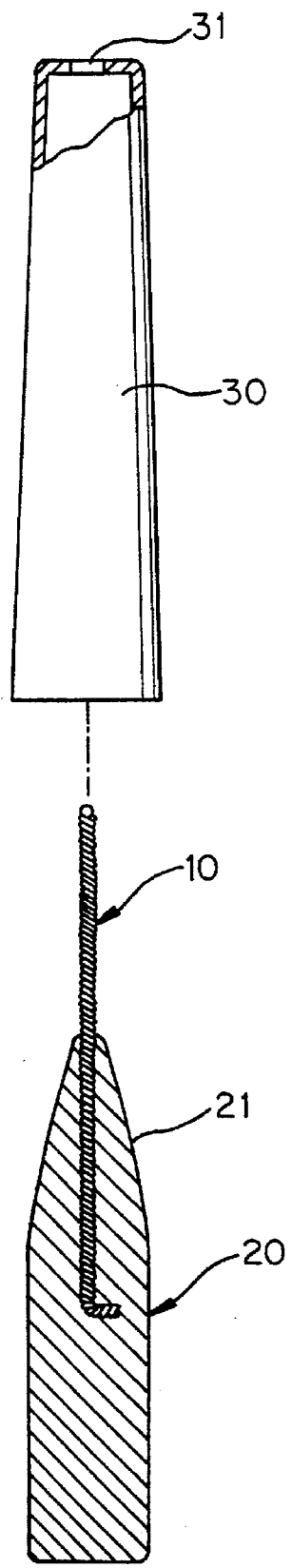
FIG. 3 is an enlarged, cutaway sectional view of the present invention.

Referring to FIGS. 1, 2 and 3, the present invention comprises an interteeth inserting portion 10 formed of spirally twisted wire of the same diameter and coated of synthetic resin, a main body 20 formed to fixedly embrace a certain length of the inter-teeth inserting portion 10, a cap 30 for allowing the main body 20 to be inserted and separated with the interteeth inserting portion 10 being covered.

The inter-teeth inserting portion 10 is constructed one end of which is bent to be firmly fixed to main body 20 and the other end of which is covered with synthetic resin in the form of curvature during its coating process.

The main body 20 is formed one end of which is inclined at a certain slope to have a slope side 21. The main body is formed cylindrically for easy grasping but may be formed in a multi-angled column, i.e., triangle, rectangle or hexagon.

Figure 4:
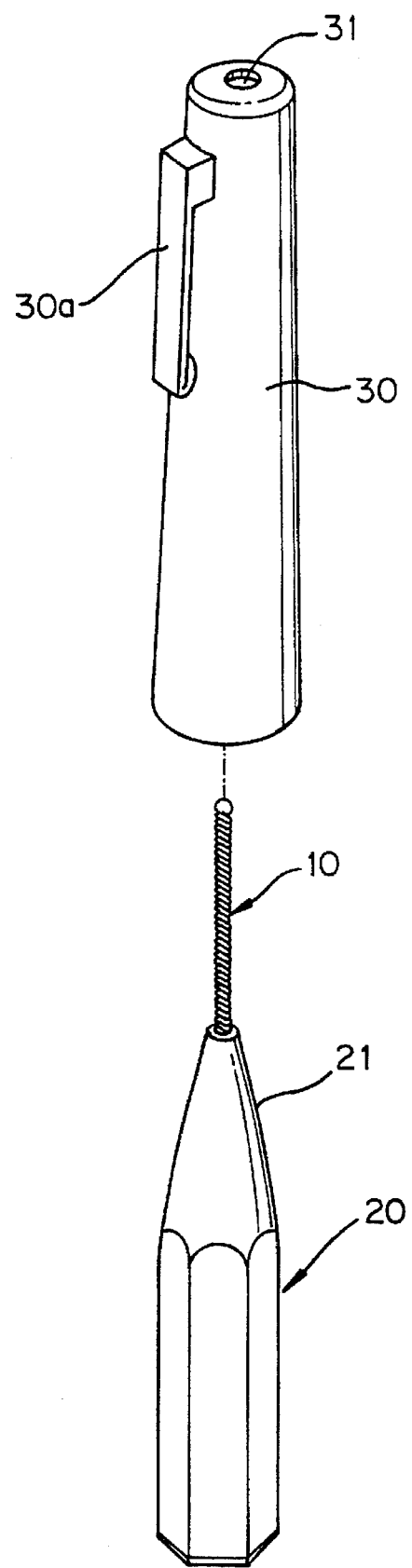
FIG. 4 is a perspective view of a modification of the present invention.

The cap 30 has a vent 31 at its upper end and an opened lower end, and is cylindrical and hollow. According to the shape of main body 20, the cap may be formed in a variety of multi-angled columns, i.e., triangle, rectangle or a hexagon, The inner surface of the cap 30 is formed in the same shape of the outer surface of main body 20 so that they are fit with each other. For a modification of the present invention, as shown in FIG. 4, a clip 30a may be formed on the outer surface around the top of the cap 30 in order to easily carry the toothpick.

In short, in the present invention constructed as above, a wire is twisted to maintain a strong elasticity, and the outer surface of the wire is covered with synthetic resin in order to remove food leftover stuck between teeth sanitarily. In removing foreign material, the space between teeth is not affected, preventing the tooth tissues and gums from being hurt. This can suppress odontological disease. Furthermore, the toothpick of the present invention can be kept semipermanently and is easy to carry, is sanitary and can have a great effect on environmental protection.

What is claimed is:

1. A toothpick comprising:
   an inner-teeth inserting portion having a metal wire spirally twisted and having an overall circumferential surface covered with synthetic resin; and
   a main body fixed to one end of said inter-teeth inserting portion for grasping
   wherein said circumferential surface has a uniform maximum diameter along its length.

2. The toothpick as in claim 1, wherein the main body includes a circular cross-section.

3. The toothpick as in claim 1, further comprising a cap for allowing said interteeth inserting portion to be inserted and separated from said main body when it is covered.

4. The toothpick as in claim 3, wherein said cap has a clip on its top outer surface.

5. The toothpick as in claim 1, wherein the main body includes a multi-angled cross-section.

6. The toothpick of claim 1, wherein said spirally twisted metal wire includes a first portion received and secured in the main body and a second portion protruding from an upper end of the main body.

7. A reusable toothpick comprising:

a main body including an upper end; and a spirally twisted metal wire including a first portion received and secured in the main body and a second portion protruding from the upper end of the main body;

wherein at least the second portion of the metal wire is coated with a synthetic resin; and wherein the second portion of the metal wire is adapted to be inserted between teeth.

8. The toothpick of claim 5, wherein the first portion of the metal wire includes a bent segment to facilitate securing of the metal wire within the main body.

9. The toothpick of claim 5, wherein the main body includes a circular cross-section.

10. The toothpick of claim 5, wherein the main body includes a multi-angled cross-section.

11. The toothpick of claim 5, further comprising a removable cap covering at least the second portion of the metal wire when the cap is inserted on the main body.

12. The toothpick of claim 9, wherein the cap includes a clip on an upper outer surface thereof.

* * * * *